United States Patent
Roberts et al.

[19]
[11] Patent Number: 6,123,076
[45] Date of Patent: Sep. 26, 2000

[54] HYDROPHOBIC BARRIER FOR FILTERS AND FILTER MEDIA

[75] Inventors: Keith A. Roberts, St. Paul, Minn.; Michael R. Spearman, The Woodlands, Tex.; John H. Burban, Lake Elmo, Minn.; Majid Zia, White Bear Township, Minn.; Rochelle M. Mickschl, St. Paul, Minn.

[73] Assignee: Porous Media Corporation, St. Paul, Minn.

[21] Appl. No.: 09/075,001

[22] Filed: May 8, 1998

Related U.S. Application Data

[60] Provisional application No. 60/046,045, May 9, 1997, and provisional application No. 60/047,438, May 22, 1997.

[51] Int. Cl.⁷ .................................................. A62B 23/02
[52] U.S. Cl. ................................ 128/205.29; 128/205.27
[58] Field of Search ......................... 128/205.29, 205.27, 128/204.18, 206.15, 206.16, 201.13

[56] References Cited

U.S. PATENT DOCUMENTS

| | | | |
|---|---|---|---|
| 3,782,083 | 1/1974 | Rosenberg | 55/491 |
| 4,215,682 | 8/1980 | Kubik et al. | 128/205.29 |
| 4,871,352 | 10/1989 | Tran . | |
| 4,874,659 | 10/1989 | Ando et al. | 428/221 |
| 4,902,423 | 2/1990 | Bacino . | |
| 5,158,077 | 10/1992 | Sundstrom | 128/205.27 |
| 5,195,527 | 3/1993 | Hicks | 128/205.12 |
| 5,213,096 | 5/1993 | Kihlberg et al. | 128/205.12 |
| 5,232,478 | 8/1993 | Farris . | |
| 5,320,096 | 6/1994 | Hans | 128/205.29 |
| 5,330,559 | 7/1994 | Cheney et al. . | |
| 5,350,443 | 9/1994 | von Blucher et al. . | |
| 5,472,481 | 12/1995 | Jones et al. | 96/15 |
| 5,474,599 | 12/1995 | Cheney et al. . | |
| 5,486,411 | 1/1996 | Hassenboehler, Jr. et al. . | |
| 5,538,545 | 7/1996 | Dauber et al. . | |
| 5,540,756 | 7/1996 | Hoppitt et al. . | |
| 5,540,761 | 7/1996 | Yamamoto . | |
| 5,549,735 | 8/1996 | Coppom . | |
| 5,573,577 | 11/1996 | Joannou . | |
| 5,582,632 | 12/1996 | Nohr et al. . | |
| 5,587,005 | 12/1996 | De Marco . | |
| 5,590,644 | 1/1997 | Rosenkoetter | 128/201.13 |
| 5,592,933 | 1/1997 | Zucchi | 128/201.13 |
| 5,829,428 | 11/1998 | Walters et al. | 128/200.24 |

*Primary Examiner*—Aaron J. Lewis
*Assistant Examiner*—Teena Mitchell
*Attorney, Agent, or Firm*—Marshall & Melhorn

[57] ABSTRACT

A filter is disclosed having a layer of electret filter media or triboelectric filter media immediately adjacent or in intimate contact with one, or both sides, of a layer of hydrophobic media. Such filter is placed in communication with the upstream and/or downstream side of a mechanical electronic or electrostatic filter to solve problems present in the prior art. Additionally, a medical ventilator filter and system using such a filter is disclosed.

16 Claims, 10 Drawing Sheets

HYDROPHOBIC BARRIER FOR FILTERS AND FILTER MEDIA

CROSS REFERENCE TO RELATED APPLICATIONS

This application is claiming the benefit, under 35 U.S.C. §119(e), of the Provisional Applications filed May 9, 1997 and May 22, 1997 under 35 U.S.C. §111 (b), which were granted Ser. Nos. 60/046,045 and 60/047,438 respectively. The provisional applications, Ser. Nos. 60/046,045 and 60/047,438 are incorporated herein by reference.

BACKGROUND OF THE INVENTION

1. Field of the Invention

The present invention relates to filter assemblies of the mechanical, electronic and electrostatic nature. More particularly, the invention relates to a water repellent barrier for use with mechanical, electronic and electrostatic filter assemblies to prevent water droplets from entering the filter assembly and lessening the effectiveness of, or destroying, the filter media.

Most particularly, the present invention relates to a hydrophobic barrier placed in sealing engagement with the upstream or intake and/or downstream or exhaust side of a filter assembly.

2. Description of the Prior Art

Generally, filter assemblies fall into one of three categories. Mechanical filters, electronic filters, and electrostatic (non-powered electronic) air filters. A mechanical filter generally consists of a flat, or pleated, mat of fibers (the "filter media") contained in a supporting frame. This type of filter removes particles from the air passing through it by collecting them as they impact on individual fibers, or are too large to pass between fibers. The percentage of particulates trapped determines the filter's overall efficiency, e.g. four percent, twenty percent, fifty percent, or eight-five percent, etc. The typical "furnace filter" will be of a low resistance with very low efficiency. A "high tech filter", the HEPA (High Efficiency Particle Arrestor) filter will be a high resistance filter with a high particulate removal efficiency.

The second category of filter assemblies is that of the powered electronic air cleaner. Powered electronic air cleaners draw air in through a front section which electrically charges the incoming particles with a positive charge, and then passes these particles between a series of plates which are alternately positive and ground. Positive particles in the air stream are repelled away from the positive plates over to the grounded plates where they collect. Because of their very open configuration, such units naturally have a very low resistance to air flow.

The third category of filter apparatus is the non-powered electronic or electrostatic air filter. Electrostatic air filters have either an electret media or a triboelectric media.

An electret media is a filter media having plastic fibers which are permanently charged by heating and cooling them in an electric field during manufacture. The fibers then contain both positive and negative charges on the surface.

A triboelectric filter media contains at least two different types of polymer fibers and are charged by the rubbing of the fibers during manufacture or use. One fiber becomes positively charged, and the other becomes negatively charged. A good discussion of the different types of air filters and examples thereof is contained in U.S. Pat. No. 5,549,735 issued Aug. 27, 1997 to Rex R. Coppom. The specification of the Coppom patent is specifically incorporated herein by reference.

Those skilled in the art are coming to realize that all three of these types of filter assemblies or units can suffer a loss of efficiency, or other problems, if the media therein is contaminated by water droplets. Water droplets, as opposed to water vapor, can saturate or discharge the media depending on the type of filter, and result in a loss in efficiency.

The problems caused in mechanical type filters by being impacted by water droplets, such as might occur in a home heating system installed in a home having an "ultrasonic" humidifier discharging fine water droplets into the air, have been found to be of three types. First, if the media is not hydrophobic, the fibers in the media may swell, and cause an increased flow resistance.

Second, the impact of water droplets may "wash off" previously captured particles if the size thereof is smaller than the pore structure of the filter. Third, if a mechanical filter with a tight pore structure is involved, the filter can plug up.

In an electronic filter, a different type of problem exists. The problem of "popping" when wet with regard to electronic filters is discussed in the U.S. Pat. No. 5,232,478 issued Aug. 3, 1993 to Richard W. Farris. The specification of the Farris patent is herein specifically incorporated by reference. As described in said patent, cleaning conventional permanent electronic air filters involves saturating a collecting cell in water. If the air filter is reinstalled in the furnace and energized before the collecting cell has completely dried, high voltage arcing will occur through the filter media between the high voltage grid and the grounded grills. While such arcing is not necessarily damaging, it creates a loud and annoying "popping" sound which can continue for an appreciable length of time.

It is believed that the continuation of such "popping" for a considerable length of time may be due to water droplets circulating in the heating system and/or water droplets entering the heating system from ultrasonic humidifiers. Also, even when dry, it is believed that water droplets entering the heating system from ultrasonic humidifiers will occasionally cause this annoying "popping" sound.

While the solution presented in said U.S. Pat. No. 5,232,478 is generally satisfactory for preventing the "popping" after a complete immersion of the filter in water, during the time the filter is wet, it is grounded, and has no cleaning efficiency. Thus, it is not an entirely satisfactory solution. Further it provides no answer as to how to prevent water droplets from circulating in the heating system, either from the air cleaner itself, or from ultrasonic humidifiers. Therefore, those skilled in the art of electronic filters have continued to search for a satisfactory solution for removing water droplets from a heating system in which it is installed.

Electrostatic filters, used widely in the medical and other areas, depend on the positive and negative charges appearing on the fibers to attract oppositely charged particles. It is believed that water droplets trapped by an electret, or triboelectric media, or any other media that can be charged, or that depends on charging as the main mechanism for particle removal, will short out or neutralize the media in the areas where the water droplets lodge, resulting in a great decrease in efficiency as long as the water droplets are present in the filter. Thus, it would be very desirable to have a barrier to remove these water droplets.

SUMMARY OF THE INVENTION

A hydrophobic media is placed in communication with the upstream and/or downstream side of a mechanical, electronic, or electrostatic filter to solve the problems in the art described above.

In one embodiment of the present invention, a hydrophobic media is placed in sealing communication with a common mechanical type filter.

In another embodiment of the invention, a hydrophobic media is placed in intimate contact with a filter media of the type used in mechanical filters.

In another embodiment of the invention, a layer of hydrophobic media is placed upstream and/or downstream of an electronic air filter.

In another embodiment of the present invention, a hydrophobic media is placed upstream of an electret filter media.

In yet a further embodiment of the invention, a hydrophobic media is provided in intimate contact with an electret filter media.

In another embodiment of the present invention, a hydrophobic media is placed upstream of a triboelectric filter media.

In a further embodiment of the invention, a hydrophobic media is provided in intimate contact with a triboelectric filter media.

In a still further embodiment of the present invention, a rectangular filter media having an upstream side and a downstream side has a hydrophobic media placed in sealing communication with the upstream side of the filter media.

In a further embodiment of the invention, media of the foregoing nature is manufactured in a circular or any other geometrical shape and has a layer of hydrophobic media in intimate contact therewith.

In a further embodiment of the present invention, a pleated filter media is provided having a layer of electret or triboelectric filter media, with a layer of hydrophobic media placed on the upstream and/or downstream side of the filter media.

In a further embodiment of the invention, a tubular pleated filter is provided wherein the pleated media includes a layer of filter media in intimate contact with a layer of hydrophobic media on the upstream and/or downstream side of the pleated media.

In a further embodiment of the invention, a tubular filter is provided having a layer of filter media surrounded by a layer of hydrophobic media on the upstream and/or downstream side of the filter media.

In a further embodiment of the invention, an air filter assembly is provided for use in automotive or marine applications which includes at least one layer of a filter media and at least one layer of a hydrophobic media in sealing communication with the upstream side of said filter media.

In yet another embodiment of the present invention, a pleated panel type filter is provided having a filter media mounted within a supporting frame member and having a layer of hydrophobic media in sealing communication with the upstream side of said pleated filter media.

Thus, it is an object of the present invention to provide a filter media for use in mechanical, electronic, or electrostatic filter assemblies which includes a layer of suitable filter media having a layer of hydrophobic media in intimate contact therewith on the upstream and/or downstream side of the filter media.

Another object of the present invention is to provide a mechanical filter assembly including at least one layer of a filter media and a layer of a hydrophobic media in sealing communication with the upstream side of said filter media.

Another object of the present invention is to provide an electronic filter assembly having at least one layer of a hydrophobic media in sealing communication with the upstream side and/or downstream side of said electronic filter.

It is a still further object of the present invention to provide an electrostatic filter of the type having an electret or triboelectric filter media, and including a layer of hydrophobic media in sealing communication with the upstream and/or downstream side of the electret or triboelectric media.

Another object of the present invention is to provide a system for conditioning air in which a layer of hydrophobic media is provided in sealing communication with the filter media or air filter assembly used in the heating system to remove water droplets therefrom.

Another object of the present invention is to provide a medical ventilator filter having a layer of electret or triboelectric filter media in intimate contact with a layer of hydrophobic media.

A further object of the present invention is to provide a medical ventilator system having filters of the foregoing nature.

Further objects and advantages of this invention will be apparent from the following description and appended claims, reference being made to the accompanying drawings forming a part of the specification, wherein like reference characters designate corresponding parts in the several views.

It is to be understood that the present invention is not limited in its application to the details of construction and arrangement of parts illustrated in the accompanying drawings, since the invention is capable of other embodiments, and of being practiced or carried out in various ways within the scope of the claims. Also it is to be understood that the phraseology and terminology employed herein is for the purposes of description, and not of limitation.

DESCRIPTION OF THE PREFERRED EMBODIMENT

Generally speaking, with regard to mechanical filters, the present invention contemplates the placement of a layer of hydrophobic media made of any suitable material upstream and/or downstream of any suitable mechanical type filter such as a furnace filter, an automotive or marine air filter, a filter for electronic enclosures and the like. This may involve attaching the layer of hydrophobic media directly to the upstream and/or downstream side of the filter body. If the mechanical filter is suitably sealed in a filter housing, the hydrophobic media may be placed at any suitable distance from the upstream or downstream side of the mechanical filter as long as all the air flow passing through the filter must first pass through the upstream hydrophobic media, and all the air flow that has passed through the filter must flow through the downstream hydrophobic media, if present.

In certain applications, such as where back flow or reversal of flow may occur, it may be advantageous to place the hydrophobic media downstream of a filter, such as a mechanical filter. The placement downstream may be in addition to a layer of hydrophobic media placed upstream, if desired.

Figures 1, 2, 3:
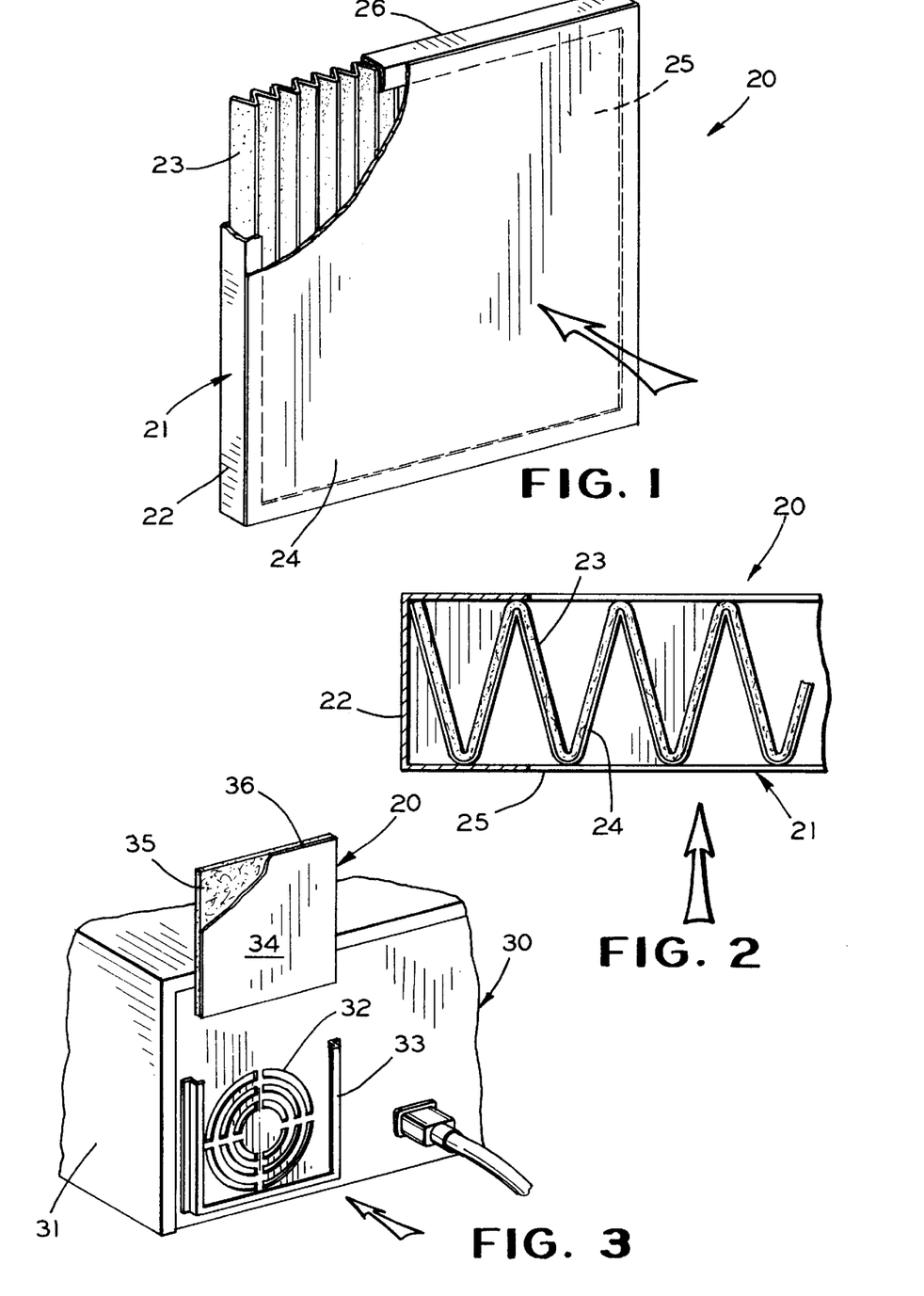
FIG. 1 shows a perspective view of the construction of the present invention embodied in one type of mechanical filter.
FIG. 2 is a view similar in part to FIG. 1 showing a modification of the present invention.
FIG. 3 is a perspective view showing the construction of the present invention embodied in an enclosure filter.

Referring now to FIG. 1, a mechanical type filter 20 is shown. By way of illustration, the mechanical filter 20 is embodied in a furnace filter 21. The furnace filter 21 is of the type well known in the art and has a rectangular channel type support frame 22 forming the four sides of the filter, and a pleated filter media 23 contained by the frame. The filter media illustrated may be any of the mechanical type filter media well known in the art, of the woven or non-woven type. A sheet of hydrophobic media 24 is sealingly affixed on the upstream side 25 of the filter 21 by attachment to the support frame 22. If desired, a similar layer of hydrophobic media could be attached to the downstream 26 of the filter 21.

The filter media illustrated in FIG. 1 is a single layer of pleated filter media. The modification of the invention illustrated in FIG. 2 shows a pleated filter media 23 having the layer of hydrophobic media 24 in intimate contact with, or immediately adjacent, the filter media 23, instead of attached to the frame 22. Either version of the mechanical filter 20 may be satisfactory depending on the application. It can be understood that any of the well known filter media in the art may be used for filter media 23 and any of the many hydrophobic medias known in the art can be used for the hydrophobic media layer 24.

In accordance with the present invention, the hydrophobic media may include various fibrous materials which are woven or non-woven and in sheet form. The hydrophobicity of the substrate may be imparted through the application of a polymeric coating onto or over the fibrous surfaces of the substrate or may be inherent in the substrate itself. The substrate may consist of one or more multiple layers of the same or different material. The substrate materials may include, but are not limited to, compounds selected from the group consisting of mineral wool, glass, quartz, stainless steel, silica, titania, carbon oxides, boron oxides, polyester, nylon, teflon, acrylic copolomer, polyether sulfone, polysulfone, polypropylene, textile fibers, textile fabrics, or any inherently hydrophobic material. Any material which can be treated with hydrophobic solutions or compounds may also be used. The preferred substrate is a non-woven sheet of glass fibers having a controlled pore structure.

The hydrophobicity of the filter media may be imparted to the substrate through the application of polymeric coatings or films to the substrate. All conventional techniques and compositions for imparting hydrophobic properties onto a fibrous substrate are suitable for use in the present invention. For example, the hydrophobicity may be accomplished through the utilization of silicone resins, polymeric siloxanes, polytetrafluoroethylene, or polymeric fluoroaliphatic esters. The compounds are applied to the substrate and polymerized to form a hydrophobic coating or film. Additionally, it is recognized in the art that specific combinations of polymers are suitable for forming hydrophobic articles. Examples include the use of either polytetrafluoroethylene or polytrifluorochloroethylene and silicone resins sinter bonded to a fibrous substrate. Also, U.S. Provisional Patent Application filed on Mar. 18, 1997 in the name of Keith Roberts, and entitled "An Antiwetting Composition for Fabrics and Fibrous Substances", herein incorporated by reference, utilizes a polymeric fluoroaliphatic ester and a silicon resin in a dispersion which is a applied to the substrate and subsequently polymerized to form a hydrophobic article. All other conventional combinations of polymers recognized in the art are suitable for forming the hydrophobic media of the present invention.

Referring now to FIG. 3, there is shown an electronic or other enclosure 30 embodying the construction of the present invention. By way of illustration, the electronic enclosure illustrated is a computer housing 31 having a ventilation opening 32 provided therein. A frame member 33 fixedly attached proximate the ventilation opening 32 in the computer housing 31 holds a mechanical type filter 20 embodying the construction of the present invention in front of the upstream side of the ventilation opening 32. It can be understood by those skilled in the art that, depending on the application, the filter 20 could also be held on the downstream side of the ventilation opening 32. In this embodiment, the mechanical filter 20 is a rectangular filter element 34 consisting of a layer of any suitable filter media 35 and an adjoining layer of a suitable hydrophobic media 36.

Figure 4:
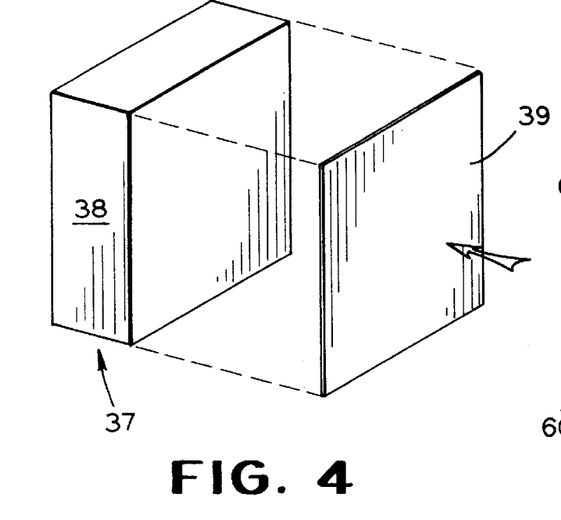
FIG. 4 shows the construction of the present invention embodied in an electronic filter.
Figure 5:
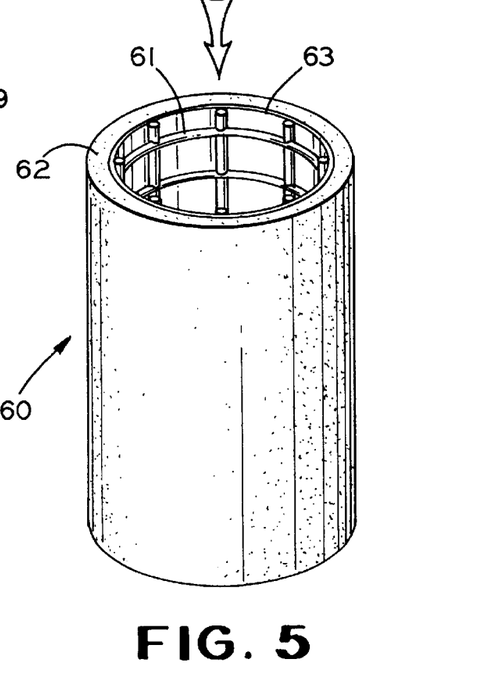
FIG. 5 is a top perspective view of a cylindrical embodiment of an element for a room air purifier.
Figure 5A:
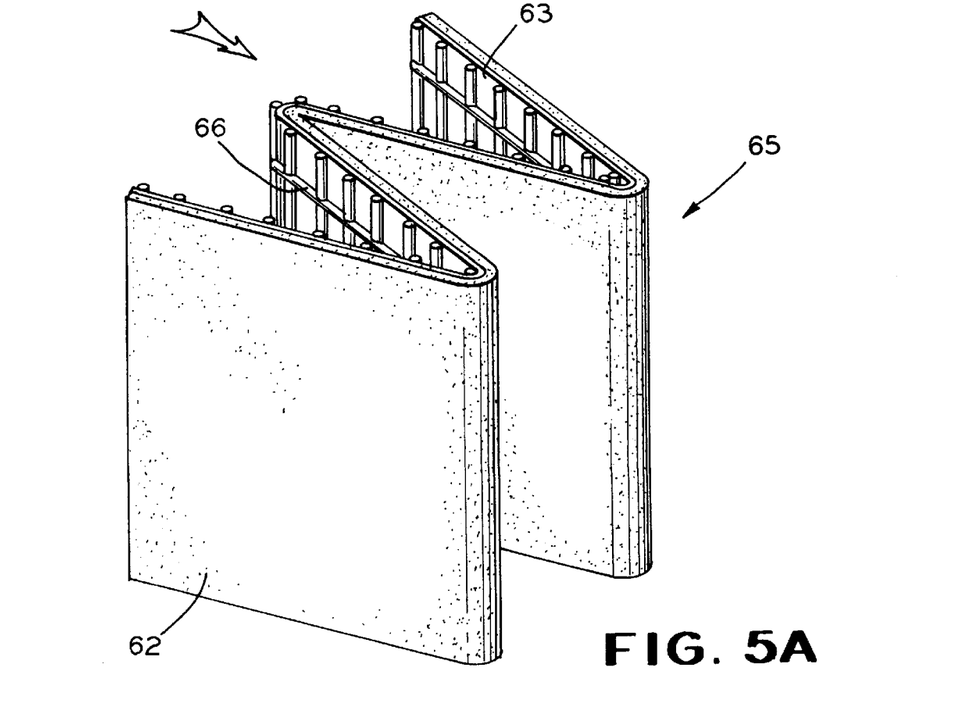
FIG. 5a is a top perspective view of a pleated embodiment of an element for a room air purifier

FIGS. 4, 5 and 5A relate to embodiments of the present invention directed to electronic filters. As mentioned previously, the problem with electronic filters is not saturation of a filter media.

As discussed above, the problem with electronic air filters is the problem of "popping" when wet, and the speed with which the electronic filters can be dried after washing. It is believed that electronic filters can be dried faster after washing if the droplets, which remain on the plates after washing, and thereafter enter the air stream when the system in which the electronic filter is utilized is activated, are removed from the air stream as soon as possible so they do not continue to pass through the filter. Also, the problem of "popping" during normal operation can be minimized if droplets introduced into the air circulating through such filters, such as by "ultrasonic" humidifiers, and by other factors operating in the environment, can be removed. This can be accomplished by placing a layer of any suitable hydrophobic media in suitable communication with the upstream side of an electronic filter. All conventional hydrophobic media may be used upstream of any known electronic filter to eliminate or reduce the above-mentioned problems.

Referring to FIG. 4, there is shown an electronic air cleaner 37 having a collector cell 38. Upstream of the collector cell is a layer of suitable hydrophobic media 39. The hydrophobic media 39 is in sealing communication with the upstream side of the collector cell 38. The media 39 may be physically attached to the collector cell 38 by adhesive or other suitable means or may be placed slightly upstream from the collector cell 38 such that the opening in a furnace duct leading to the electronic air cleaner as long as substantially all the air going through the electronic air cleaner 38 must pass first through the hydrophobic media 39.

Referring now to FIGS. 5 and 5A there are shown portions of tubular filters and pleated filters such as those used in room air purifiers which may be such as those disclosed in U.S. Pat. No. 5,549,735 issued Aug. 27, 1996 to Rex R. Coppom. As disclosed in the Coppom patent the tubular filter 60 has a layer of suitable filter material 62 surrounding a tubular grid 61. It is believed that interposing a layer of suitable hydrophobic material 63 between the tubular grid 61 and the filter material 62 may alleviate problems present in these devices.

Similarly, as shown in FIG. 5A a pleated filter 65 has a layer of filter media 62 over a pleated grid 66. It is felt beneficial to interpose a layer of hydrophobic media 63 between the pleated grid 66 and the filter media 62.

The remainder of the drawing figures deal with electrostatic filters and the problems encountered when water droplets are deposited on the media of the electrostatic filter thereby discharging or neutralizing the media.

The media used for electrostatic filters may be a media whose plastic fibers are either permanently charged by heating and cooling them in an electric field during manufacturing (electret media), or a media having the property of becoming electrostatically charged during manufacturing or after by friction between dissimilar fibers (triboelectric media). It is believed that both the electret and triboelectric media electrostatic filters encounter problems when water is deposited on their fibers. The electrostatic filter may also be made of any other fibers or materials which can take a charge, and may be made of woven or non-woven webs. Non-woven webs may be such as melt blown webs, spunbond, hydro-entangled, needled webs and laminated combinations of these. The webs may be charged during manufacture or after. U.S. Pat. Nos. 5,244,482 and 5,486,411 contain a discussion of the charging of webs and the specifications thereof are specifically incorporated by reference.

Figure 6:
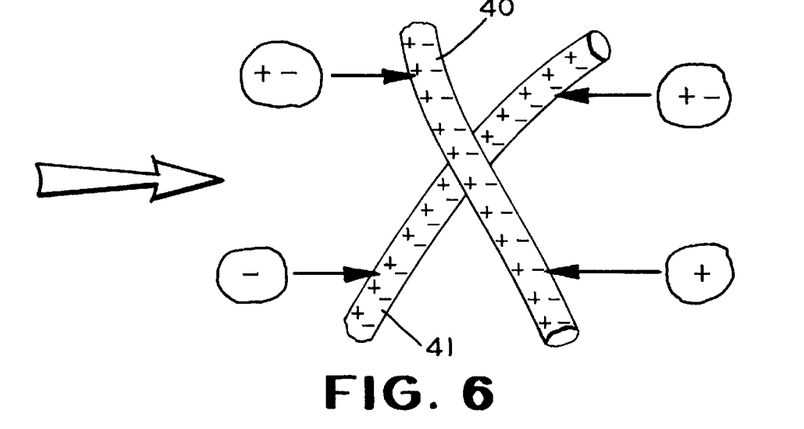
FIG. 6 is a diagrammatic view of two electrified fibers in an electret filter media.

Referring to FIG. 6, there is shown a diagrammatic view on an enlarged scale of two fibers of an electret type media. A first fiber 40 and a second fiber 41 are illustrated. Electret media is produced by generating an electric field during manufacture across the media thickness with positive and minus electrodes, corona discharge, etc. The fibers after this treatment then contain both positive and negative charges on the surface as illustrated. Both first fiber 40 and second fiber 41 are similarly charged. If air containing water droplets flows over the fiber so charged, it is believed that the situation illustrated in FIG. 7 occurs.

Figure 7:
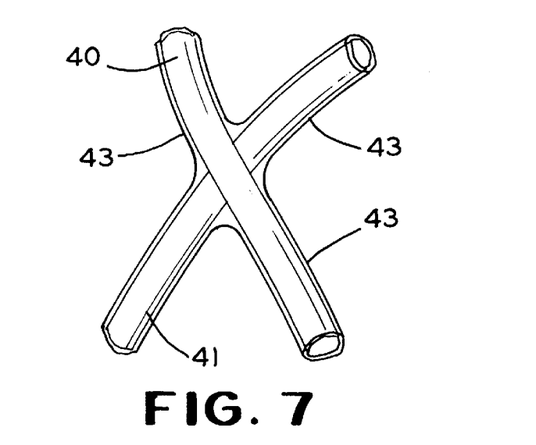
FIG. 7 is diagrammatic view similar in part to FIG. 5 showing how fibers in electret media are effected by water droplets being deposited thereon.

Water droplets impact the fibers and spread over the surface of the fibers, forming the water film 43. The water film 43 effectively shorts out or shields the charge resulting in the surface of the fiber (actually water) being uncharged. As water film covers more and more of the fibers 40 and 41, the electret filter media has less and less efficiency.

Figure 8:
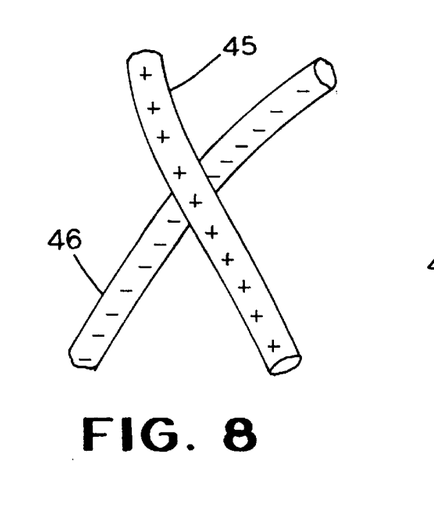
FIG. 8 is a diagrammatic view of two electrified fibers in a triboelectric filter media.

Referring now to FIG. 8, triboelectric filter medias have a similar loss of efficiency, but for different reasons. Triboelectric filters contain at least two different types of polymer fibers and are charged by the rubbing together of the dissimilar fibers during manufacture, or after. One fiber becomes positively charged, and the other negatively charged. By way of illustration there is shown a third fiber 45 which has become positively charged, and a fourth fiber 46 which is negatively charged.

Figure 9:
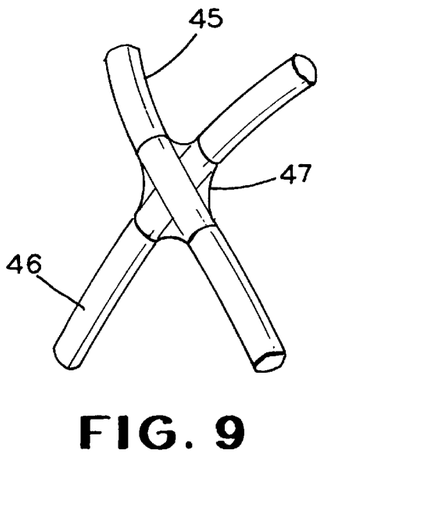
FIG. 9 is a view, similar in part to FIG. 8, showing the effect of water droplets on triboelectric filter media fibers.

As illustrated in FIG. 9, due to the difference in charging, water droplets contained in the air stream passing over a triboelectric fiber do not impact and form a water film on the fiber but, instead, bridge gaps between positive and negative fibers. There is shown a water droplet 47 lodged between third fiber 45 and fourth fiber 46. The water droplet 47 spans third fiber 45 and fourth fiber 46 and produces a conductive pathway between the fibers. Because of this, the fibers 45 and 46 become neutralized or uncharged. A neutralized area of the triboelectric filter media will not attract particulates and, therefore, is totally ineffective. As more and more water droplets lodge between fibers, larger and larger areas of the triboelectric filter media become ineffective, resulting in a loss of efficiency.

It has been found that, depending upon the application, the proper placement of a layer of hydrophobic media on the upstream side and in some cases on the downstream side of the layer of the filter media solves this problem in the art. In general, as hereinafter illustrated, a layer of hydrophobic media may be in close or intimate contact with a layer of filter media regardless of the shape of the filter media, or whether the filter media is flat or pleated. Alternately, if the hydrophobic media is not in intimate or in close contact, and the application is a proper application, a layer of hydrophobic media may be wrapped around the layer of filter media. As long as the layer of hydrophobic media is in a sealing relationship or communication with the filter media, the purposes of the present invention will be achieved. It should be understood that "in a sealing relationship or communication" simply means that substantially all the air flow entering the upstream side of a sheet of filter media must pass through the hydrophobic barrier which is on the upstream side of the filter before entering the filter media.

Likewise, if an application requires a layer of hydrophobic media on the downstream side of the filter media, such as when back pulsing or backflow is present, this simply means that substantially all the air which has passed through the filter media must pass through the hydrophobic media. Virtually any application where an electrostatic filter is to be used may benefit from the present invention.

Figure 10:
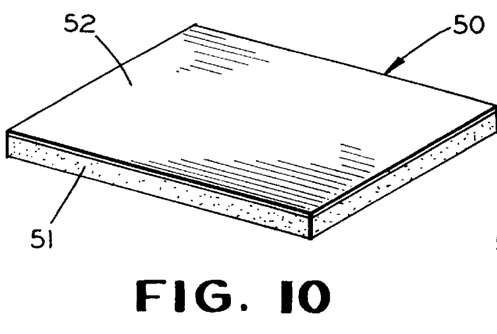
FIG. 10 is a perspective view of a rectangular electrostatic filter embodying the construction of the present invention.
Figure 11:
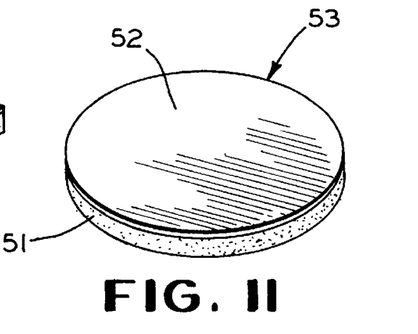
FIG. 11 is a perspective view of a circular electrostatic filter embodying the present invention.

Referring to FIG. 10, there is shown a rectangular filter 50 constructed of a layer of any practical filter media 51 and a layer of any practical hydrophobic media 52. The filter may also be made circular, as shown in FIG. 11, or in any other desired geometrical shape. Rectangular filters 50 and circular filters 51 have been found useful in a wide variety of applications such as medical applications and electronic applications.

Figure 12:
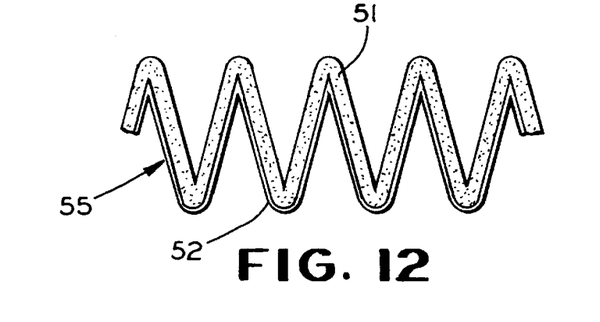
FIG. 12 is an elevational view of a pleated filter embodying the construction of the present invention.
Figure 13:
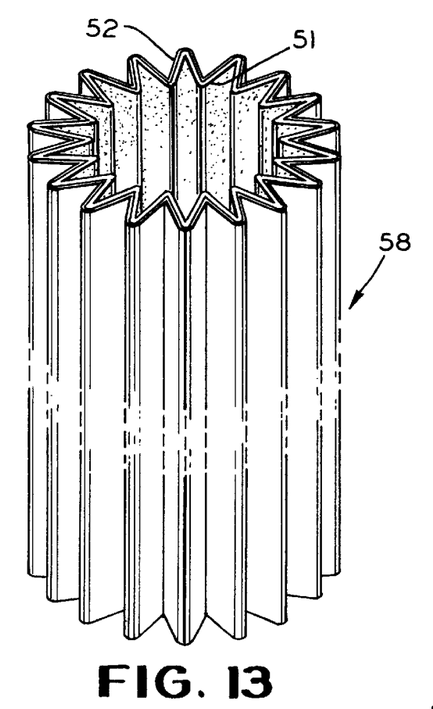
FIG. 13 is a perspective view of a pleated tubular filter embodying the construction of the present invention.
Figure 15:
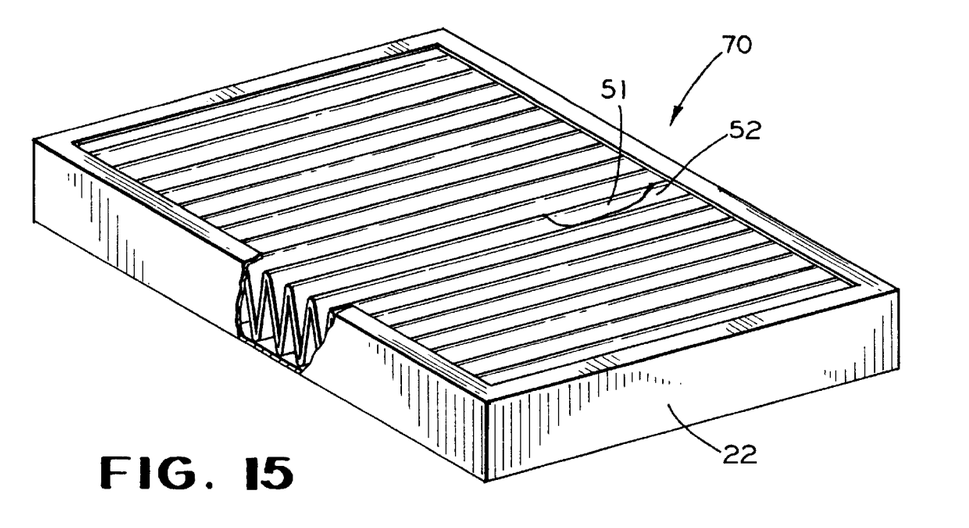
FIG. 15 is a perspective view of a pleated panel filter embodying the construction of the present invention.

A pleated filter 55, such as shown in FIG. 12, is formed of a layer of filter media 51 pleated with a layer of hydrophobic media 52. The pleated filter media may be used in the pleated tubular filter 58 shown in FIG. 13 in the pleated panel filter 70 shown in FIG. 15, or in any other application where a pleated media is used.

Figure 14:
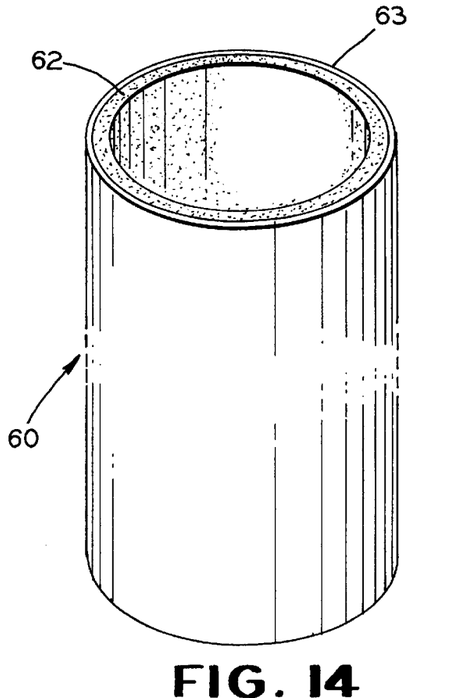
FIG. 14 is a perspective view of a tubular filter embodying the construction of the present invention.

The present invention may also be practiced in applications which require tubular filters. Shown in FIG. 14 is a tubular filter 72 comprising a layer of hydrophobic media 52 in intimate or close contact with a layer of filter media 51. Depending upon whether the flow is in to out, or out to in, the hydrophobic media 52 may be placed on the outside or the inside of the filter media 51. In some applications it is contemplated that a layer of hydrophobic media 52 may be placed on both sides of the layer of filter media 51.

As with mechanical filters and certain electronic filters the filter media may be made of a wide variety of materials such as polytetrafluoroethylene, polyproplene, glass, wool, polyester, nylon, Dacron, cotton, other organic fibers and steel. The filter media may be made out of woven or non-woven fibers.

Figure 16:
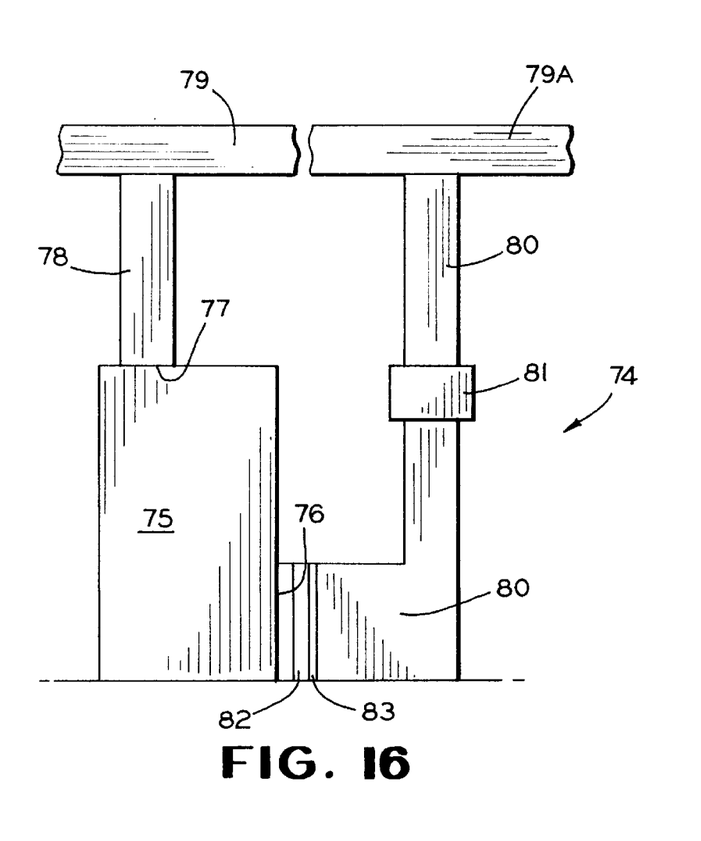
FIG. 16 is a diagrammatic view of a heating system embodying the construction of the present invention.

The present invention as embodied in a system for conditioning air is illustrated in FIG. 16. The system for conditioning air 74 may include such as a suitable conditioning unit 75 for heating or cooling the air as desired. The conditioning unit 75 has an air intake 76 in fluid communication with an air exhaust 77. An exhaust duct 78 takes the conditioned air from the conditioning unit 74 and transports it to the common duct 79. Common duct 79 distributes the conditioned air to the structure in which the conditioning system 74 is installed. Second common duct 79A withdraws air from the structure and passes it through intake duct 80 to the conditioning unit 75. A humidifier 81 of any type well known in the art may be mounted to the intake duct 80. An electronic or electrostatic air cleaner 82 is interposed between the intake duct 80 and the air intake 76 of the conditioning unit 75. A layer of hydrophobic media 83 is in sealing communication with the electronic or electrostatic air cleaner 82 to remove any water droplets from the air and thus reduce or eliminate the aforementioned problems.

Figure 17:
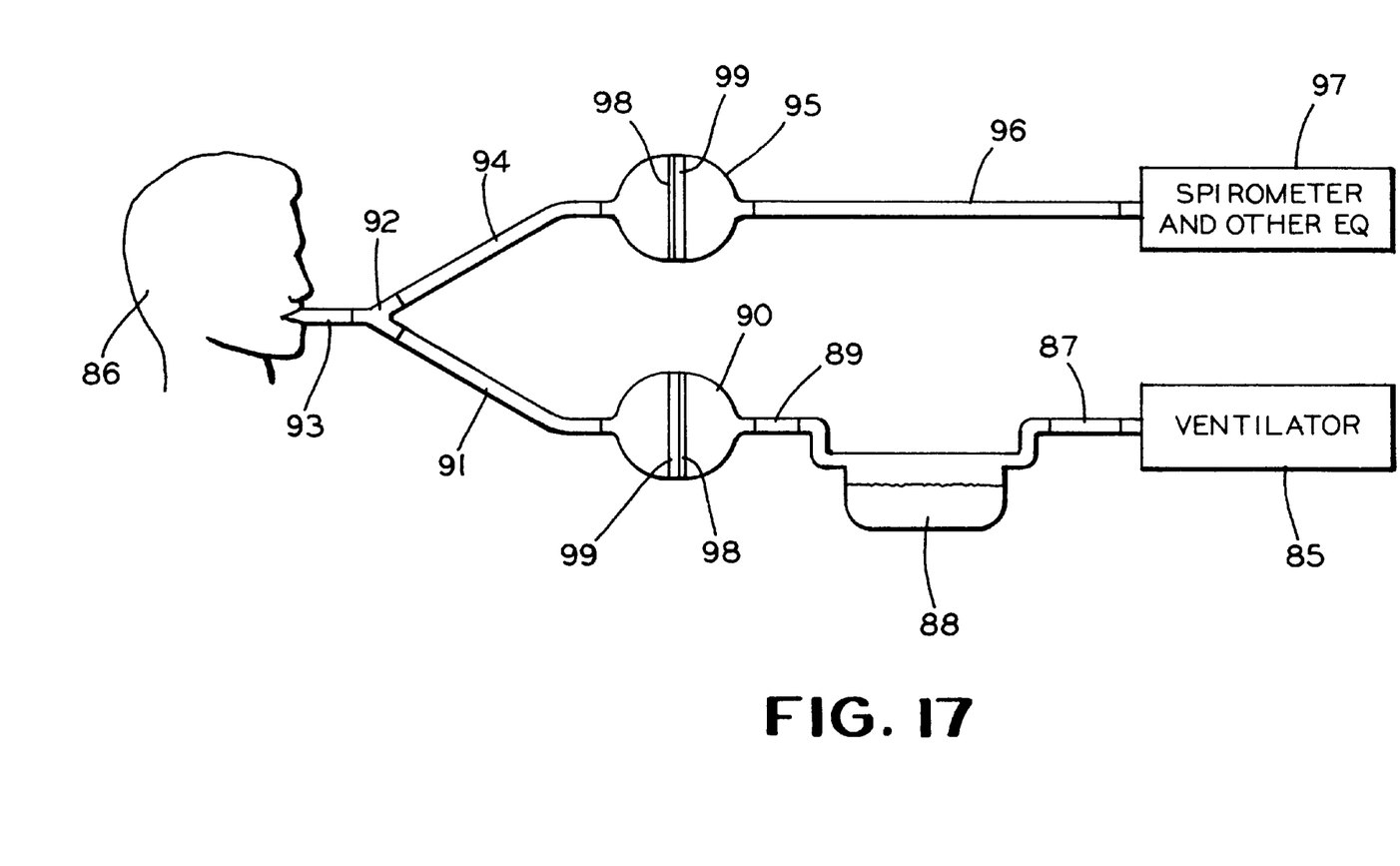
FIG. 17 is a diagrammatic view of medical respiratory system embodying the construction of the present invention.
Figure 18:
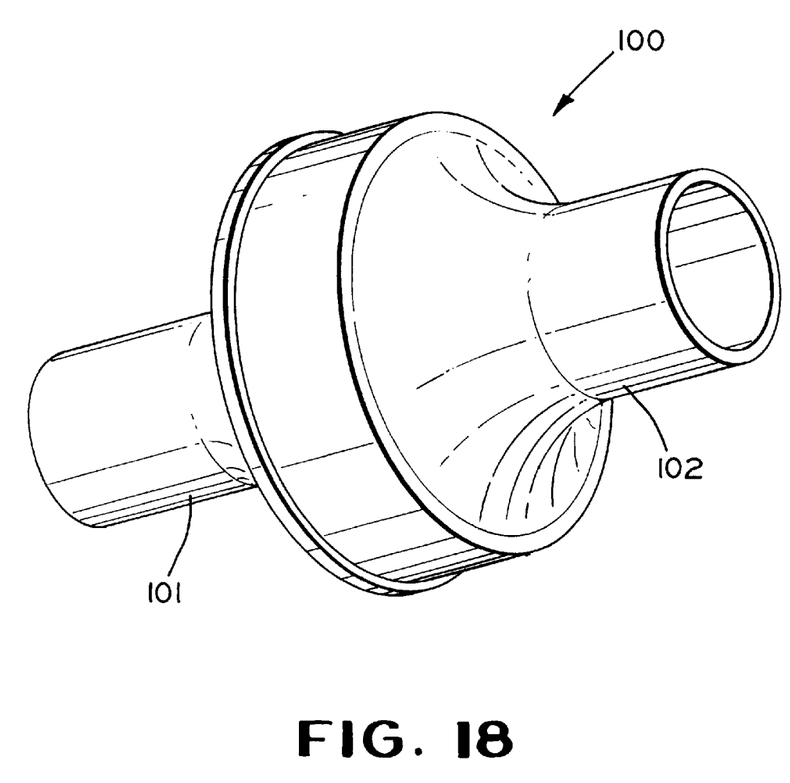
FIG. 18 is a perspective view of a medical ventilator filter embodying the construction of the present invention.

The present invention has been found particularly useful in medical applications. A typical medical respiratory system is shown in FIG. 17. A ventilator 85 which supplies pressurized and/or conditioned air to a patient 86 is connected through a first conduit 87 to a water bath humidifier 88. A second conduit 89 connects the water bath humidifier 88 to an inspiratory filter 90. The filter 90 is referred to as an inspiratory filter because it is in the inhalation or intake or upstream side of the circuit from the patient 86. A third conduit 91 connects the inspiratory filter 90 to a Y connector 92. The patient 86 communicates with the Y connector through a mouth piece 93. The Y connectors 92 are well known in the art and serve the purpose of letting the patient 86 breathe freely from the ventilator 85 when inhaling, but diverts air being exhaled by the patient, thereby preventing it from traveling back to the ventilator, due to the positive pressure in the ventilation circuit.

Instead, air being exhaled by the patient 86 travels out through the Y connector 92 to the expiratory portion of the circuit which includes fourth conduit 94 connecting the Y connector 92 in fluid communication with the expiratory filter 95. In turn, the expiratory filter 95 is connected by fifth conduit 96 to the spirometer 97 and other necessary equipment. Because the respiratory filter 90 is downstream of the water bath humidifier which generates humidity which includes liquid droplets, the hydrophobic media 98 is placed on the side toward the water bath humidifier 88 (also called the machine side) so as to prevent water droplets as well as dirt from contaminating the electrostatic filter media 99.

However, the expiratory or exhalation circuit in which the expiratory filter 95 is placed is in a location where the filter can capture patient's sputum and exhaled medication. For this reason the hydrophobic barrier 98 is placed on the patient's side to protect the equipment on the exhalation side of the patient from these droplets.

Referring now to FIGS. 18–22 there is shown a medical ventilator filter 100 that may serve as the inspiratory filter 90, (see FIG. 17) the expiratory filter 95, (see FIG. 17) or a main flow filter (not shown) for medical applications. While in all the applications previously described, whether for mechanical, electronic, or electrostatic filters, the addition of the hydrophobic media will increase the pressure drop and will need to be taken into account in the design of the filter, in medical applications, because of the small size of the filters, this consideration becomes more important since adding a hydrophobic barrier to the electret or triboelectric media will add pressure drop if there is not enough surface area.

Figure 19:
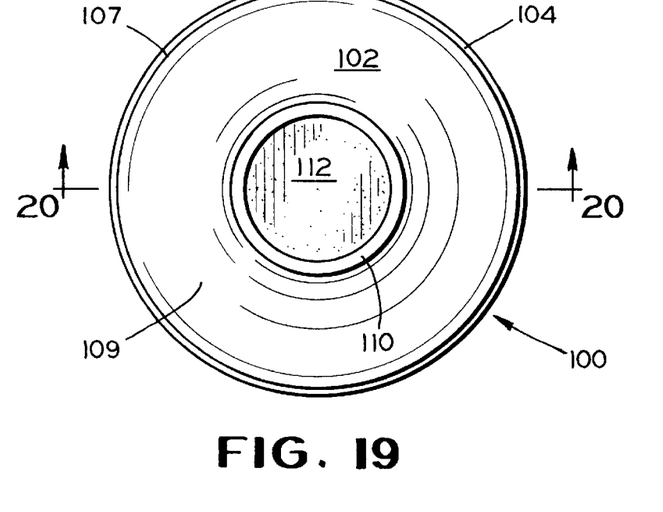
FIG. 19 is a top plan view of the construction shown in FIG. 18.
Figure 20:
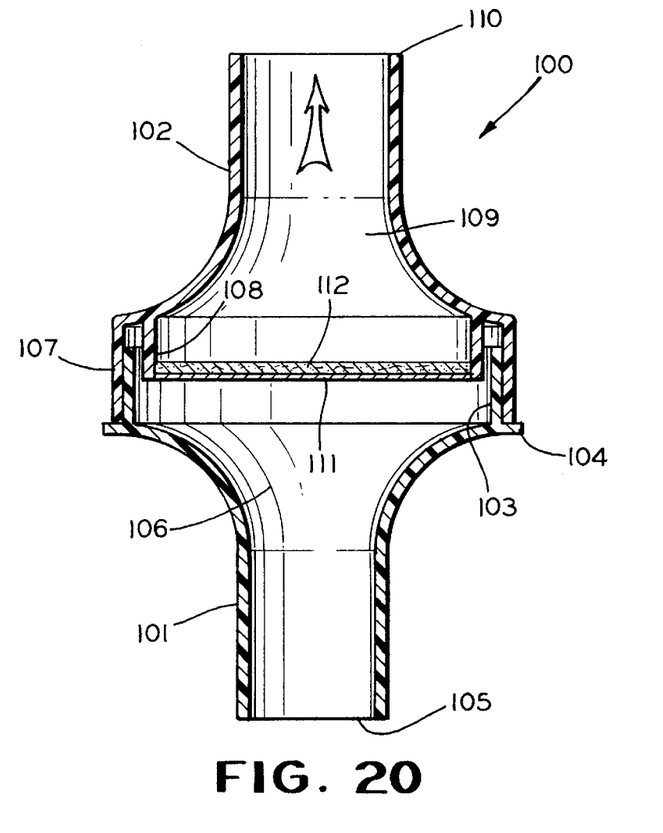
FIG. 20 is a sectional view, taken in the direction of the arrows, along the section line 20—20 of FIG. 19.

A desirable flow resistance for pressure drop for medical applications is approximately less than 2.0 cm $H_2O$ at 60 LPM. A typical diameter ventilator filter using an electrostatically charged media is a approximately 2.0". However, when the hydrophobic media is added to the electret or triboelectric media in a medical ventilator filter, due to its small size, pressure drops of about 4.0 cm $H_2O$ are not uncommon. This is approximately double the desired flow resistance for this application. Therefore we want to increase the surface area by at least double to cause the pressure drop to fall in the range of 2 cm $H_2O$. To double the surface area of a circular filter, the resulting increase in diameter is to about 3.3". A construction of the medical ventilator filter 100 with a flat hydrophobic barrier and a flat disk of electret filter media is shown in FIGS. 19 and 20.

The lower filter housing 101 has a circular upstanding wall 103 of slightly smaller outer diameter than the diameter of the lower filter housing itself, resulting in a circular ridge 104 around the periphery of the housing. To complete the lower filter housing 101 there is an intake portion 105 and a plenum portion 106.

The upper filter housing 102 has a first downstanding wall 107 having an inside diameter substantially the same as the outside diameter of the circular upstanding wall 103, and an outside diameter smaller than the outside diameter of the lower filter housing so that a short portion of the ridge 104 will extend past the downstanding wall 107 when the upper filter housing is assembled to the lower filter housing.

A second circular downstanding wall 108 of an outside diameter slightly smaller than the inside diameter of the upstanding wall 103 is provided proximate the first upstanding wall 107. The height of downstanding wall 108 is less than the height of first downstanding wall 107 and the space or gap between the first downstanding wall 107 and the second downstanding wall 108 is such that the circular upstanding wall 103 fits therebetween. Upper filter housing 102 has a plenum portion 109 and an outlet portion 110. A circular disk of hydrophobic media 111 is attached to the inside periphery or lower edge of the downstanding wall 108. Immediately downstream of the hydrophobic media or barrier 111 is a circular disk of electret media 112, also attached to the inner pherphery or lower edge of the downstanding wall 108. Care must be taken that both the hydrophobic barrier and the electret media are completely attached along their entire pherphery to the downstanding wall 108 so that no air may pass through the inlet 105 and out through the outlet 110 without passing through both the electret media 112 and the hydrophobic media 111.

It can be easily understood by those skilled in the art that the positions of the hydrophobic barrier 111 and the electret media 112 may be reversed if needed depending upon the application such as discussed in connection with FIG. 17. Alternately, the intake end and the outlet end of the filters may simply be reversed if the connections in a system permit this.

Figure 21:
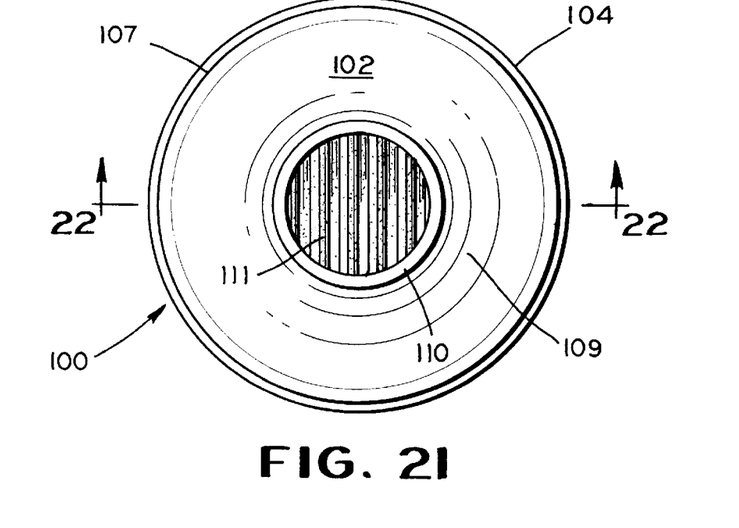
FIG. 21 is a top plan view of a modification of the construction shown in FIG. 18.
Figure 22:
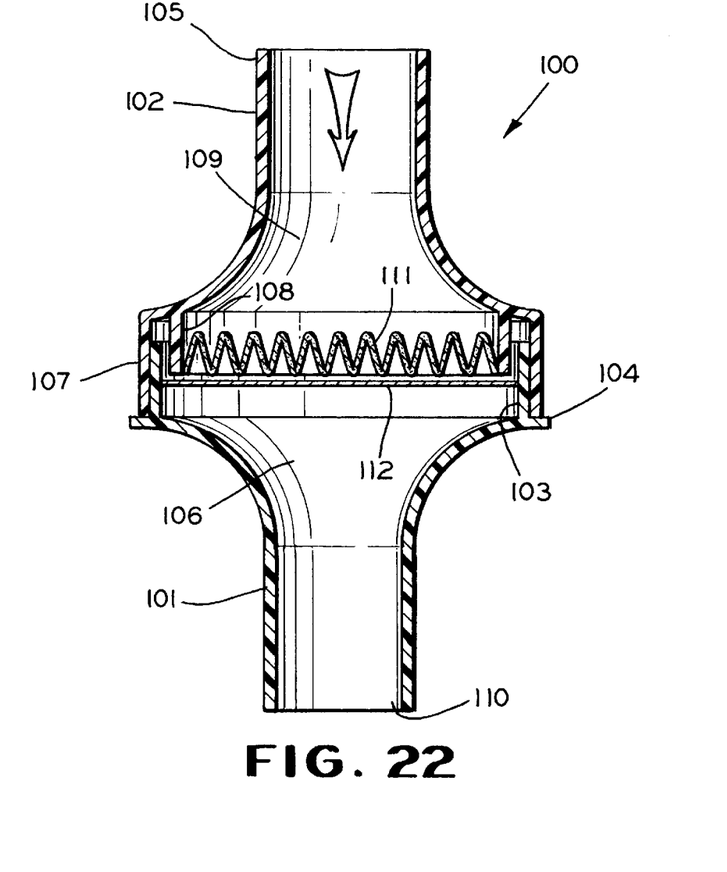
FIG. 22 is a sectional view taken in the direction of the arrows, along the section line 21—21 of FIG. 20.

Referring to FIGS. 21–22, a modification of the filter of FIG. 20 is shown. The construction of the filter is identical to that shown in FIG. 20 except for the mounting of the hydrophobic barrier or media 111 and the electret media 112. Therefore identical reference numerals have been used. However, the flow has been reversed for ease of illustration.

In this case, even with the addition of the hydrophobic barrier, the diameter of the electret media 112 may be returned to its diameter of 2" to achieve the less than 2.0 cm $H_2O$ at 60 lpm flow resistance. This is because the pleating of the hydrophobic media 111 provides the greater surface area needed so as not to cause the pressure drop attendant with the flat disk. This allows the hydrophobic barrier to be provided in a housing slightly larger than 2" outside diameter instead of the 3.3" diameter which is necessary with the flat layer of hydrophobic media 111. This saves manufacturing costs and makes for an economical installation.

To achieve this, the pleated hydrophobic media 111 is sealingly mounted to the pherphery of the downstanding wall 108 while the flat disk of electret media is sealingly mounted to the interior pherphery of the upstanding wall 103. This also provides for a slightly larger surface area of the electret media 112.

If a polymeric media is being used for the hydrophobic barrier 111 and/or the electret media 112 these may sonically welded in place. If a paper type media is being used they may be adhesively held in place or bonded in place. In the manufacturing process after the hydrophobic barrier 111 and the electret media 112 are attached to the second downstanding wall 108 and the upstanding wall 103 respectively, the lower filter housing 101 and the upper filter housing 102 will be sonically welded together to completely seal the interior of the filter housing.

Figure 23:
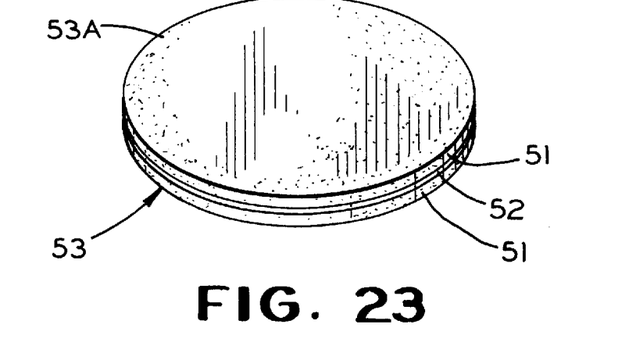
FIG. 23 is a perspective view of a circular filter embodying a further modification of the present invention.

Referring to FIG. 23, a modification of the present invention is shown. In some applications, it has been found desirable, for aesthetic purposes, to place the layer of hydrophobic media between two layers of electret or triboelectric media. There is shown a circular filter 53 having a layer of hydrophobic media 52 sandwiched between two layers of filter media 51.

Figure 24:
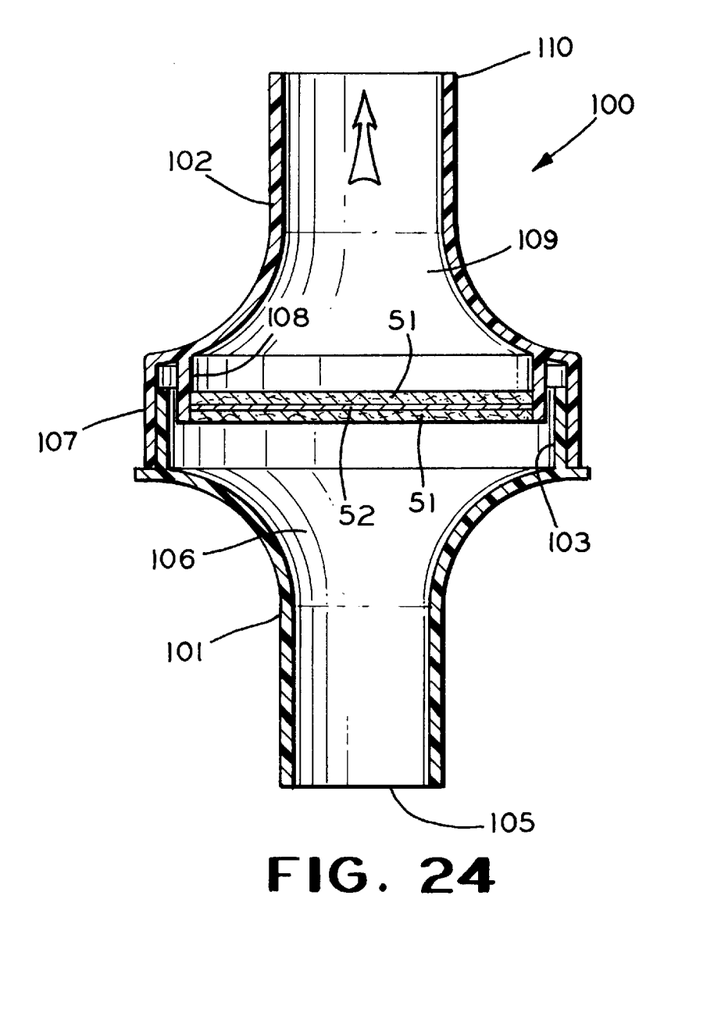
FIG. 24 is a view similar in part to FIG. 20, but having the construction of FIG. 23 mounted therein.

There is shown in FIG. 24 a medical ventilator filter assembly 100 similar to that shown in FIG. 20, but having the circular filter 53 illustrated in FIG. 23 mounted therein. The circular filter 53 is bonded, adhesively attached, or otherwise fastened about its' edge region 53A to the downstanding wall 108 in a sealing communication. The other features of the medical ventilator filter assembly 100 shown in FIG. 24 may be identical to construction shown in FIG. 20. For ease of illustration, identical reference numerals have been used.

Thus, by carefully studying the problems presented by water droplets entering mechanical, electronic, and electrostatic type filters, a novel solution to problems in the art has been obtained.

What is claimed is:

1. A medical ventilator filter, said filter including:
   a) a lower filter housing portion of a predetermined diameter, said lower filter housing including:
      i) a circular upstanding wall proximate the upper end of said lower filter housing portion, the outer diameter of said circular upstanding wall being slightly smaller than the diameter of said lower housing portion;
      ii) a ridge formed between the upstanding wall and the outer diameter of said lower housing portion; and
   b) an upper housing portion of a predetermined diameter, said upper housing including:
      i) a first circular down standing wall, the inner diameter of said first down standing wall portion being substantially the same as the outer diameter of said upstanding circular wall of said lower housing portion;
      ii) a second down standing wall, the outer diameter of said second down standing wall being less than the inner diameter of said circular upstanding wall portion of said lower housing portion, and less than the diameter of said first down standing wall;
      iii) a sheet of hydrophobic media sealingly mounted to said second down standing wall, and;
      iv) a sheet of filter media mounted to said second down standing wall immediately adjacent said sheet of hydrophobic media.

2. The filter defined in claim 1, wherein said sheet of hydrophobic media is mounted to the lower periphery of said second down standing wall.

3. The filter defined in claim 1, wherein said sheet of filter media is mounted to said second down standing wall upstream of said sheet of hydrophobic media.

4. The filter defined in claim 1, wherein said sheet of filter media is mounted to said second down standing wall downstream of said sheet of hydrophobic media.

5. The filter defined in claim 1, wherein said sheet of filter media is a sheet of electret media.

6. The filter defined in claim 1, wherein said sheet of filter media is a sheet of triboelectric media.

7. A medical ventilator filter, said filter including:
   a) a lower filter housing portion of a predetermined diameter, said lower filter housing including;
      i) a circular upstanding wall proximate the upper end of said lower filter housing portion, the outer diameter of said circular upstanding wall being slightly smaller that the diameter of said lower housing portion,
      ii) a ridge formed between the upstanding wall and the outer diameter of said lower housing portion, and
   b) an upper housing portion of a predetermined diameter, said upper housing portion including:
      i) a first circular down standing wall, the inner diameter of said first down standing wall being substantially the same as the outer diameter of said upstanding circular wall of said lower housing portion,
      ii) a second down standing wall, the outer diameter of said second down standing wall being less than the inner diameter of said circular upstanding wall portion of said lower housing portion, and less than the diameter of said first down standing wall, c) a sheet of pleated hydrophobic media sealingly mounted to said second down standing wall, and d) a sheet of filter media mounted to said upstanding wall of said lower housing portion downstream of said sheet of hydrophobic media.

8. The filter defined in claim 7, wherein said sheet of filter media is an electret media.

9. The filter defined in claim 7, wherein said sheet of filter media is a triboelectric media.

10. A medical ventilator filter, said filter including:

a) a lower filter housing portion of a predetermined diameter, said lower filter housing including;
   i) a circular upstanding wall proximate the upper end of said lower filter housing portion, the outer diameter of said circular upstanding wall being slightly smaller that the diameter of said lower housing portion,
   ii) a ridge formed between the upstanding wall and the outer diameter of said lower housing portion, and b) an upper housing portion of a predetermined diameter, said upper housing portion including:
   i) a first circular down standing wall, the inner diameter of said first down standing wall being substantially the same as the outer diameter of said upstanding circular wall of said lower housing portion,
   ii) a second down standing wall, the outer diameter of said second down standing wall being less than the inner diameter of said circular upstanding wall portion of said lower housing portion, and less than the diameter of said first down standing wall,
   iii) a filter consisting of a layer of hydrophobic media sandwiched between two layers of electrostatic filter media fastened to said down standing wall and in sealing communication therewith.

11. The filter defined in claim 10, wherein said two layers of electrostatic filter media are an electret media.

12. The filter defined in claim 10, wherein said two layers of electrostatic filter media are a triboelectric media.

13. The filter defined in claim 10, wherein one of said two layers of electrostatic filter media is an electret media, and the other of said two layers is a triboelectric media.

14. The filter defined in claim 10, wherein said hydrophobic media is a polymeric media.

15. The filter defined in claim 10, wherein said hydrophobic media is a paper type media.

16. A medical respiratory system including seriatim:

a) a ventilator, b) a first conduit connected to said ventilator, c) a water bath humidifier connect to said first conduit, d) a second conduit connected to said water bath humidifier, e) an inspiratory filter connected to said second conduit, said inspiratory filter including:
   i) a lower filter housing portion of a predetermined diameter, said lower filter housing including;
      a) a circular upstanding wall proximate the upper end of said lower filter housing portion, the outer diameter of said circular upstanding wall being slightly smaller than the diameter of said lower housing portion,
      b) a ridge formed between the upstanding wall and the outer diameter of said lower housing portion, and
   ii) an upper housing portion of a predetermined diameter, said upper housing portion including:
      a) a first circular down standing wall, the inner diameter of said first down standing wall being substantially the same as the outer diameter of said upstanding circular wall of said lower housing portion,
      b) a second down standing wall, the outer diameter of said second down standing wall being less than the inner diameter of said circular upstanding wall portion of said lower housing portion, and less than the diameter of said first down standing wall,
      c) a sheet of pleated hydrophobic media sealingly mounted to said second down standing wall, and
      d) a sheet of filter media mounted to said second down standing wall immediately adjacent said sheet of hydrophobic media, f) a third conduit connected to said inspiratory filter, g) a Y-connector connected to said third conduit, h) a fourth conduit connected to said Y-connector, i) an expiratory filter connected to said second conduit, said expiratory filter including:

i) a lower filter housing portion of a predetermined diameter, said lower filter housing including;
   a) a circular upstanding wall proximate the upper end of said lower filter housing portion, the outer diameter of said circular upstanding wall being slightly smaller than the diameter of said lower housing portion,
   b) a ridge formed between the upstanding wall and the outer diameter of said lower housing portion, and ii) an upper housing portion of a predetermined diameter, said upper housing portion including:
   a) a first circular down standing wall, the inner diameter of said first down standing wall being substantially the same as the outer diameter of said upstanding circular wall of said lower housing portion,
   b) a second down standing wall, the outer diameter of said second down standing wall being less than the inner diameter of said circular upstanding wall portion of said lower housing portion, and less than the diameter of said first down standing wall,
   iii) a sheet of hydrophobic media sealingly mounted to said second down standing wall, and
   iv) a sheet of filter media mounted to said second down standing wall immediately adjacent said sheet of hydrophobic media, j) a fifth conduit connected to said expiratory filter, and k) a spirometer connected to said fifth conduit.

\* \* \* \* \*